United States Patent [19]

Torre

[11] Patent Number: 4,961,742
[45] Date of Patent: Oct. 9, 1990

[54] SUTURE NEEDLE HOLDING INSTRUMENT

[76] Inventor: Randall J. Torre, 842 S. Clover, San Jose, Calif. 95128

[21] Appl. No.: 328,491

[22] Filed: Mar. 24, 1989

[51] Int. Cl.⁵ .............................................. A61B 17/00
[52] U.S. Cl. .................... 606/147; 606/208; 81/319; 81/322; 81/323; 81/427.5
[58] Field of Search ................... 128/340, 321; 81/319, 81/320, 321, 322, 323, 427.5, 324; 606/208, 147, 205

[56] References Cited

U.S. PATENT DOCUMENTS

| | | | |
|---|---|---|---|
| 791,322 | 5/1905 | Clayton | 128/340 |
| 835,351 | 11/1906 | Farnell | 81/324 |
| 2,539,865 | 1/1951 | Sarvie | 81/319 |
| 2,706,987 | 4/1955 | Bramstedt | 128/340 |
| 3,417,752 | 12/1968 | Butler | 128/340 |
| 3,562,908 | 2/1971 | Rogers | 602/208 |
| 3,921,640 | 11/1975 | Freeborn | 128/321 |
| 4,282,783 | 8/1981 | Fortune | 81/427.5 |
| 4,538,485 | 9/1985 | Saila | 81/320 |

FOREIGN PATENT DOCUMENTS 0641521 6/1962 Italy .................................. 81/427.5

Primary Examiner—Randall L. Green
Assistant Examiner—Gary Jackson
Attorney, Agent, or Firm—Schroeder, Davis & Orliss Inc.

[57] ABSTRACT

A surgical instrument for holding a suture needle is provided. The instrument includes handle portions shaped to accommodate the human hand, jaws formed to securely grasp a suture needle and a latching mechanism to hold the device closed so that the physician can concentrate on manipulation of the needle. The contoured shape of the handle portions improves the ability of the surgeon to grasp and manipulate the instrument under the adverse conditions encountered during surgery.

18 Claims, 2 Drawing Sheets

SUTURE NEEDLE HOLDING INSTRUMENT

BACKGROUND OF THE INVENTION

The present invention relates generally to surgical instruments and, more particularly, to a spring-loaded plier-like instrument having grooved jaws to secure a suture needle when the jaws are closed.

In many medical procedures or emergency situations a physician is often required to close and join the edges of an incision or wound with one or more sutures by the use of a small curved needle. During the suturing process, the physician must positively grip and hold the needle while achieving maximum stability and control of the needle. This is particularly true where the tissue surrounding the incision or wound is quite thin or delicate.

There are several prior art plier-like instruments and other holding devices available for gripping and securing suture needles. Many of the prior art devices are simply specially constructed long-nosed or needle-nosed pliers which may or may not have grooves provided at the distal end of the jaws to grasp a needle. Such a plier-like device requires that a physician continuously exert a closing force on the plier handles while using the instrument. Other prior art devices comprise scissor-like devices which include a ratchet mechanism between the scissor handles to couple and lock the handles together thereby maintaining the scissor jaws in a closed configuration and securely gripping and holding a needle. The ends of the handles typically carry finger loops to facilitate grasping the device. While the locking scissor device overcomes the necessity of exerting a closing force on the handles, grasping and controlling the scissor device with the finger loops tends to detract from the physician's control of the instrument during the suturing process.

SUMMARY OF THE INVENTION

It as an object of the present invention to provide a needle holding instrument which allows a physician to achieve maximum stability of the needle through hand control during the suturing procedure.

It is another object of the present invention to provide a locking needle holding instrument which frees a physician of the necessity of exerting a closing force on the device handles during use.

In accordance with the principles of the present invention a plier-like needle holding instrument having straight handles which are contoured to fit in a physician's hand is provided. A pair of plier arms pivotally joined at a pivot bearing intermediate the ends thereof have cooperating jaw portions at their distal ends and have straight handle portions at their proximal ends. The jaws are grooved at the end thereof to receive and hold a suture needle when the jaws are closed. The handle portions are coupled together by a spring-loaded locking clip which maintains the jaws in a closed configuration when the locking clip is engaged. One of the handle portions has a recessed area on the outside aspect near the pivot end of the handle portion shaped to approximately fit a human thumb. Near the end opposite the pivot bearing, the other handle portion has a series of areas of indentation shaped approximately to accommodate the fingers of a human hand.

When the locking clip is engaged, the jaws are held in a closed configuration securely gripping a needle in the instrument. The engaged locking clip relieves the physician of the necessity to hold the instrument in a closed configuration. The contoured handle portions allow the physician to achieve maximum stability of the needle during a suturing procedure through hand control of the instrument. The control of the needle holding instrument is fully realized by the grip-like configuration of the handle portions.

DETAILED DESCRIPTION OF THE PREFERRED EMBODIMENT

Figure 1:
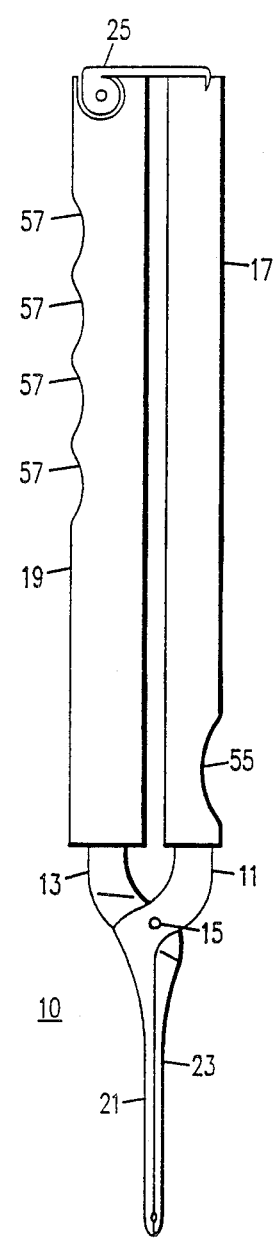
FIG. 1 is a side elevation view of a suture needle holding instrument constructed in accordance with the principles of the present invention.
Figure 2:
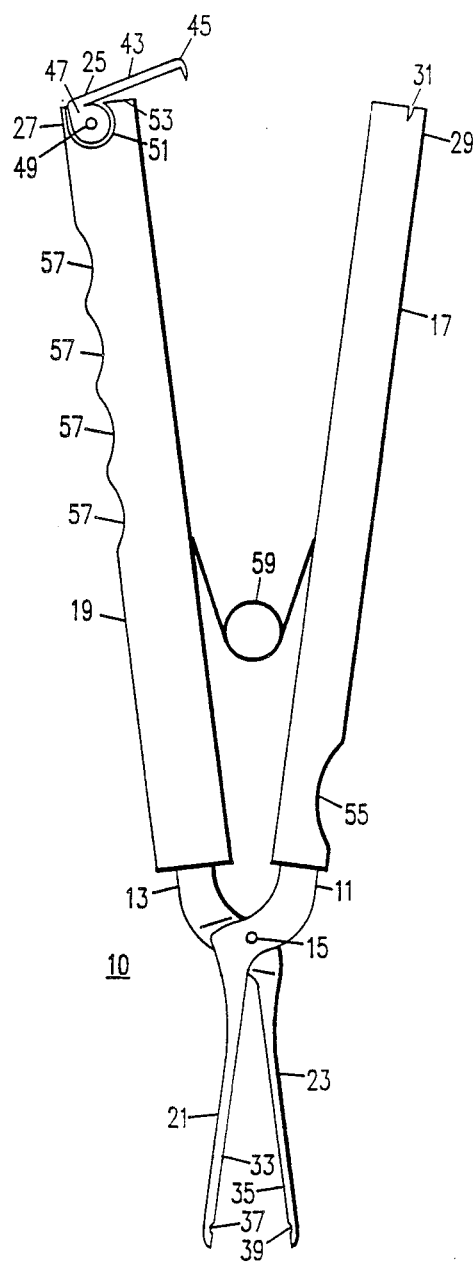
FIG. 2 is a side elevation view of the suture needle holding instrument shown in FIG. 1 in a jaws open configuration.
Figure 3A:
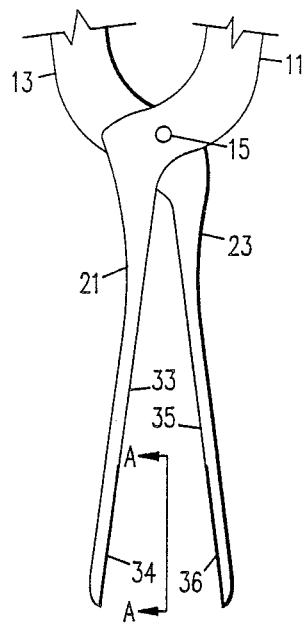
FIGS. 3A and 3B are a side view and a front view, respectively, of the jaws of the suture holding instrument shown in FIG. 1 illustrating serrated teeth to grasp a suture needle.
Figure 3B:
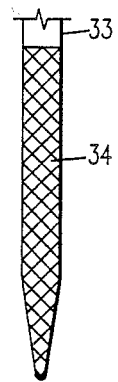

Referring now to FIGS. 1, 2, 3A, 3B and 4, a suture needle holding instrument constructed according to the principles of the present invention is provided. The suture needle holding instrument 10 comprises a pair of elongated members or plier arms 11 and 13 which intersect and are pivotally coupled together at a pivot bearing 15. The plier arms 11, 13 each have, at the proximal ends thereof, generally round and extending straight handle portions 17 and 19, respectively. The plier arm 11 extends beyond the pivot bearing 15 to form a jaw portion or jaw 21 at the distal end thereof. Similarly, the plier arm 13 extends beyond the pivot bearing 15 to form a jaw portion or jaw 23 at the distal end thereof. A spring-loaded locking clip 25 is attached at the rear end 27 (i.e., the end opposite the pivot bearing 15) of one of the handle portions 19. The locking clip 25 cooperates with an associated clip catch 31 formed in the rear end 29 of the other handle portion 17.

Figure 4:
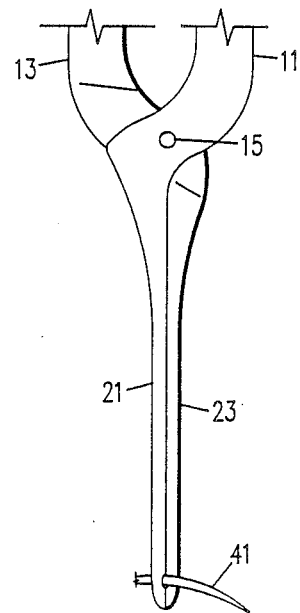
FIG. 4 is a view in perspective illustrating a suture needle secured in the jaws of the needle holding instrument shown in FIG. 1.

Each of the jaws 21, 23 are generally straight and have a generally flat inwardly facing surface 33, 35, respectively, on opposing relationship to each other. Each of the jaws 21, 23 has a transverse channel or groove 37, 39 formed in its surface 33, 35, respectively, near the front end (i.e., the end opposite the pivot bearing 15) thereof. The grooves 37, 39 are generally in alignment when the jaws of the instrument 10 are closed and are shaped and sized to receive and securely grip a suture needle 41 therein (as shown in FIG. 4). Alternatively, a portion of the inwardly facing surfaces 33, 35 extending to the tips thereof may have cross-hatched serrated teeth 34, 36, respectively, formed therein rather than the grooves 37, 39, respectively, to facilitate grasping and holding a suture needle 41.

The locking clip 25 comprises a latch bar 43 having an arcuate hook 45 at one end and a cylindrical mounting bushing 47 at the other end. The latch bar 43 is pivotally mounted on pin 49 in recess 51 formed in the rear end 27 of handle portion 19. An arcuate recess formed in the rear end 29 of handle portion 17 comprises the clip catch 31. When the handle portions 17, 19 are urged together, closing the jaws 21, 23, to a substantially parallel configuration, the latch hook 45 is engaged with the clip catch 31. The mounting bushing 47 is mounted slightly below the end surface 53 of the handle porion 19, thus when the latch hook 45 is inserted in the clip catch 31. recess, the latch bar 43 is slightly deformed and exerts a restoring force which urges the latch hook 45 out of the clip catch 31 recess. Since the clip catch 31 is curved inwardly, the latch hook 45 is held engaged until the handle portions are squeezed together allowing the latch hook 45 to disengage from the clip catch 31. The locking clip 25 is fabricated from a resilient material such as spring steel or other suitable material.

One of the handle portions 17 has a recessed area 55 on the outside aspect near the pivot bearing 15 end of the handle portion. The recessed area 55 is contoured to approximately fit a human thumb. The other handle portion 19 has several recessed or indented areas 57, three or four for example, on the outside aspect positioned from the approximate midpoint to near the rear end 27 of the handle portion 19. The indented areas 57 are shaped and positioned to accommodate the fingers of a human hand. The hand grip configuration of the handle portions 17, 19 allows the user to achieve full control of the instrument.

The suture needle holder instrument 10 is fabricated from stainless steel or other suitable material such as tungsten carbide having sufficient flexibility and corrosion resistance to allow the instrument 10 to be used in surgical procedures. The plier arms 11, 13 each may be fabricated as an integral unit in a well-known manner or, alternatively, the plier arms 11, 13 including the jaw portions 21, 23 may be integrally formed and the handle portions 17, 19 fabricated from tubular stock such as aluminum tubing and attached, such as by welding or other suitable means, to the plier arms 11, 13.

The jaws 21, 23 are opened by squeezing the handle portions together slightly allowing the latch hook 45 to disengage from the clip catch 31 and then spreading the handle portions 21, 23 apart opening the jaws 21, 23 at the distal end of the instrument 10. A light spring 59 may be attached between the handle portions 17, 19 urging the handle portions apart. When the handle portions 17, 19 are squeezed together, the locking clip 25 may be reengaged thus clamping the jaws 21, 23 together and gripping and securing a suture needle 41 in the instrument 10. If included, the spring 59 will be compressed exerting a force against the inside surfaces of the handle portions 17, 19 urging the handle portions apart and further ensuring that the locking clip 25 will remain engaged during use of the instrument 10.

Although the present invention has been described in its preferred form with a degree of particularity, it is understood that the present disclosure of the preferred embodiment has been by way of example and that numerous changes in the details of construction may be restored to without departing from the spirit and scope as hereinafter claimed.

I claim:

1. Apparatus for gripping and holding a suture needle for use during surgical procedures comprising:
   first and second elongated members;
   each of said first and second elongated members having a generally straight handle portion fixedly attached at one end thereof and a jaw at the other end thereof, said handle portions being adjacent and disposed parallel to one another when said jaws are in a closed configuration, said handle portions fabricated of aluminum;
   pivot means pivotally interconnecting said first and second elongated members intermediate the ends thereof;
   a transverse groove formed in a facing surface of each jaw near the end of each jaw, said facing surface of each jaw in opposing relationship with the facing surface of the other jaw, said grooves for receiving a suture needle and securely gripping said suture needle in said jaws when said jaws are in a closed configuration;
   locking means including a locking clip pivotally attached at the end of one of said handle portions, said locking clip adapted to engage a clip catch formed in the end of the other one of said handle portions, said locking means for releasable coupling said handle portions together, said jaws in an open configuration when said locking means is disengaged and said jaws in a closed configuration when said locking means is engaged; and
   one of said handle portions including a recessed area on the outside aspect of said handle portion near said pivot means, said recessed area contoured to approximately accommodate a human thumb and the other one of said handle portions including a plurality of indented areas on the outside aspect of said other handle jportion, each of said plurality of indented areas contoured to approximately accommodate human fingers.

2. Apparatus as in claim 1 wherein said jaws are fabricated from tungsten carbide.

3. Apparatus as in claim 1 wherein said first and second elongated members are fabricated of stainless steel.

4. Apparatus as in claim 1 further comprising spring means disposed between said handle portions providing a force urging said handle portions apart.

5. Apparatus for gripping and holding a suture needle for use during surgical procedures comprising:
   first and second elongated members;
   each of said first and second elongated members having a handle portion at one end thereof and a jaw at the other end thereof, said handle portions being adjacent one another;
   pivot means pivotally interconnecting said first and second elongated members intermediate the ends of thereof;
   a transverse groove formed in a facing surface of each jaw near the end of each jaw, said facing surface of each jaw in opposing relationship with the facing surface of each of the other jaw, said grooves for receiving a suture needle and securely gripping said suture needle in said jaws when said jaws are in a closed configuration;
   locking means including a spring-loaded locking clip pivotally attached at the end of one of said handle portions, said spring-loaded locking clip comprising a latch arm having an arcuate latch hook at one end and a mounting bushing at the other end, said mounting bushing pivotally mounted in a recess formed in the end of said one handle portion, and an arcuate recess formed in the end of said other handle portion for receiving said latch hook when said locking clip is engaged, said locking means for releasable coupling said handle portions together, said jaws in an open configuration when said locking means is disengaged and said jaws in a closed configuration when said locking means is engaged; and one of said handle portions including a recessed area on the outside aspect of said handle portion near said pivot means, said recessed area contoured to approximately accommodate a human thumb and the other one of said handle portions including a plurality of indented areas on the outside aspect of said other handle portion, each of said plurality of indented areas contoured to approximately accommodate human fingers.

6. Apparatus as in claim 5 wherein said handle portions are generally straight and are disposed parallel to each other when said locking means are engaged and said jaws are in a closed configuration.

7. Apparatus as in claim 6 wherein said handle portions are fabricated separately from said first and second elongated members.

8. Apparatus as in claim 7 wherein said handle portions are fabricated of aluminum.

9. Apparatus as in claim 7 wherein said jaws are fabricated from tungsten carbide.

10. Apparatus as in claim 6 wherein said first and second elongated members are fabricated of stainless steel.

11. Apparatus as in claim 5 further comprising spring means disposed between said handle portions providing a force urging said handle portions apart when said handle portions are in a closed configuration.

12. Apparatus for gripping and holding a suture needle for use during surgical procedures comprising:
   first and second elongated members;
   each of said first and second elongated members having a handle portion at one end thereof and a jaw at the other end thereof, said handle portions being adjacent one another;
   pivot means pivotally interconnecting said first and second elongated members intermediate the ends thereof;
   serrated teeth formed in a portion of a facing surface of each jaw extending to the end of said jaw, said facing surface of each jaw in opposing relationship with the facing surface of the other jaw, said serrated teeth for grasping and securely gripping a suture needle in said jaws when said jaws are in a closed configuration;
   locking means including a spring-loaded locking clip pivotally attached at the end of one of said handle portions, said spring-loaded locking clip comprising a latch arm having an arcuate latch hook at one end and a mounting bushing at the other end, said mounting bushing pivotally mounted in a recess formed in the end of said one handle portion and said clip catch comprising an arcuate recess formed int the end of said other handle portion for receiving said latch hook when said locking clip is engaged, said locking means for releasable coupling said handle portions together, said jaws in an open configuration when said locking means is disengaged and said jaws in a closed configuration when said locking means is engaged; and
   one of said handle portions includes a recessed area on the outside aspect of said handle portion near said pivot means, said recessed area contoured to approximately accommodate a human thumb and the other one of said handle portions including a plurality of indented areas on the outside aspect of said other handle portion, each of said plurality of indented areas contoured to approximately accommodate human fingers.

13. Apparatus as in claim 12 wherein said handle portions are generally straight and are disposed parallel to each other when said locking means are engaged and said jaws are in a closed configuration.

14. Apparatus as in claim 13 wherein said handle portions are fabricated separately from said first and second elongated members.

15. Apparatus as in claim 14 wherein said handle portions are fabricated of aluminum.

16. Apparatus as in claim 14 wherein said jaws are fabricated from tungsten carbide.

17. Apparatus as in claim 15 wherein said first and second elongated members are fabricated of stainless steel.

18. Apparatus as in claim 12 further comprising spring means disposed between said handle portions providing a force urging said handle portions apart.

* * * * *